(12) United States Patent
Westerink et al.

(10) Patent No.: US 8,882,669 B2
(45) Date of Patent: Nov. 11, 2014

(54) COMPUTER PROGRAM PRODUCT, DEVICE AND METHOD FOR MEASURING THE AROUSAL OF A USER

(75) Inventors: Joanne Henriette Desiree Monique Westerink, Eindhoven (NL); Cornelis Tuinenbreijer, Eindhoven (NL); Maria Helena Schut, Eindhoven (NL); Egidius Leon Van Den Broek, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 879 days.

(21) Appl. No.: 12/527,052

(22) PCT Filed: Feb. 11, 2008

(86) PCT No.: PCT/IB2008/050477
§ 371 (c)(1),
(2), (4) Date: Aug. 13, 2009

(87) PCT Pub. No.: WO2008/099320
PCT Pub. Date: Aug. 21, 2008

(65) Prior Publication Data
US 2010/0022852 A1   Jan. 28, 2010

(30) Foreign Application Priority Data
Feb. 13, 2007   (EP) .................... 07102207

(51) Int. Cl.
*A61B 5/02*   (2006.01)
(52) U.S. Cl.
USPC .......................................... 600/306

(58) Field of Classification Search
CPC ............... A61B 5/0002; A61B 5/0059; A61B 5/02154; A61B 5/021; A61B 5/441; A61B 5/0205; A61B 5/1102; A61B 5/085; A61B 5/0537; A61B 7/04
USPC ......... 600/300, 481–485, 500, 527–528, 533, 600/547, 306
See application file for complete search history.

(56) References Cited

U.S. PATENT DOCUMENTS 5,995,868 A   11/1999   Dorfmeister et al.
6,067,468 A * 5/2000   Korenman et al. ........... 600/547
(Continued)

FOREIGN PATENT DOCUMENTS

DE   102005058332 A1   1/2007
EP         0538739 A1   4/1993
(Continued)

OTHER PUBLICATIONS

Roth et al: "Sympathetic Activation in Broadly Defined Generalized Anxiety Disorder"; Journal of Psychiatric Research, Vol. 42, No. 3, Feb. 2008, pp. 205-212.
(Continued)

*Primary Examiner* — Patricia Mallari
*Assistant Examiner* — Vasuda Ramachandran

(57) ABSTRACT

Computer program product for processing GSR (galvanic skin response) signals, which when run on a computer controls the computer to estimate a level of arousal, or at least a change in the level of arousal, of a user, provided with an algorithm that is configured to control a computer to calculate a third or higher central moment of a recorded GSR signal and to derive an estimation of the level of arousal from said third or higher central moment.

17 Claims, 2 Drawing Sheets

(56) References Cited

U.S. PATENT DOCUMENTS

| | | | |
|---|---|---|---|
| 6,190,314 B1 | 2/2001 | Ark et al. | |
| 6,487,442 B1* | 11/2002 | Wood | 600/515 |
| 6,546,378 B1 | 4/2003 | Cook | |
| 6,843,774 B2* | 1/2005 | Foust et al. | 600/549 |

FOREIGN PATENT DOCUMENTS

| | | |
|---|---|---|
| EP | 1352610 A1 | 10/2003 |
| RU | 2166280 C2 | 4/2001 |

OTHER PUBLICATIONS

Van Den Broek et al: "Computing Emotion Awareness Through Facial Electromyography"; Downloaded From eidetic.ai-ru.nl/egon/publications/pdf/HCI2006.pdf on Sep. 18, 2006, 12 page document.

Biopac Systems: "Electrodermal Response (EDR) With an MP System"; Application Note, Updated Aug. 18, 2006, Downloaded From www.seas.upenn.edu/courses/belab/be100/BioPac%20Sensors/GSR.pdf on Sep. 18, 2006, 6 page document.

Biopac Systems, Inc.:"AcqKnowledge Software Guide for Life Science Research Applications"; Reference Manual Version 3.8.5 for MP Hardware/Firmware and AcqKnowledge Software on PC running Windows 2000 or Windows XP or Mac OS X, Downloaded From teachinglabs.med.utoronto.ca/DTL_Area/AcqKnowledge%20Software%20Guide.pdf on Sep. 17, 2006, (375 total pages—excerpts of pp. 1-7, 296-336 and 367-375 included).

10010.Testing for Differences Between Two Groups: t Test, Downloaded From http://web.uccs.edu/1becker/spss80/ttest.htm on Sep. 18, 2006, 13 page document.

\* cited by examiner

COMPUTER PROGRAM PRODUCT, DEVICE AND METHOD FOR MEASURING THE AROUSAL OF A USER

FIELD OF THE INVENTION

The invention relates to a computer program for processing GSR (galvanic skin response) signals, which when run on a computer controls the computer to estimate a level of arousal.

Also, the invention relates to an arousal measuring device, provided with a GSR (galvanic skin response) sensor for recording GSR signals from a user.

Furthermore the invention relates to a method for estimating a level of arousal.

BACKGROUND OF THE INVENTION

In the field, applications are known that try to automatically measure the emotional state of a user. This can for example be of interest to improve human-computer interaction. Examples of such products are 'Journey to wild divine' of the 'Wild Divine' company, and 'FREEZE-FRAMER'®, of the company HeartMath. Both products measure e state of relaxation of the user.

There are different ways to measure particular emotions in an automated way. For example, it is known that changes in arousal/excitement/relaxation (relaxation being the opposite of arousal/excitement) affect the ANS (autonomous nervous system), which in turn alters the psychological/emotional state of a subject. This may be expressed in various physiological parameters, such as for example heart rate, blood pressure, respiration rate and GSR (galvanic skin response). Measuring techniques include measuring the tension of the muscles, recording the (ir)regularity of the heart rate and measuring the conductance of the skin. The latter is also known as GSR (galvanic skin response) or SCR (skin conductance response).

A GSR (or SCR) signal is a continuous signal that can be derived from the skin by a GSR sensor that measures the electrical resistance of the skin. In a known method that uses GSR the GSR signal is averaged over a certain time period such that noise is reduced and an estimation of the relative level of arousal over that time period is obtained. Another method detects peaks in the recorded GSR signal within a certain time period. A disadvantage of these methods is that they need an inconvenient period of calibration in advance to obtain baseline measurements that are used as reference values. Only after obtaining the baseline measurements an estimation of the level of arousal can be measured.

SUMMARY OF THE INVENTION

A goal of the invention is to be able to estimate the level of arousal of a person in a convenient way.

In a first aspect, this goal and/or other goals can be achieved individually or in combination by a computer program product for processing GSR (galvanic skin response) signals, which when run on a computer controls the computer to estimate a level of arousal, or at least a change in the level of arousal, of a user, provided with an algorithm that is configured to control a computer to calculate a third or higher central moment of a recorded GSR signal and to derive an estimation of the level of arousal from said third or higher central moment.

It has been found from experiments, that by using a calculated third or higher order moment of a recorded GSR signal, a fair insight in the level of arousal of a subject can be obtained, or at least in the change of the level of arousal of the subject. These third or higher moments are statistical formulas of a higher order and can be derived from the GSR signal, whereas these calculations can be made without needing baseline measurements, i.e. without needing a period of calibration. This allows for instant use of the arousal measuring product, which is convenient for the user. Also a quick automated form of feedback can be made possible after/while the GSR (galvanic skin response) signals are recorded. For example, the user may receive direct feedback that is adjusted to the user's state of arousal/relaxation.

In an embodiment, skewness (third order moment about the mean) or kurtosis (fourth order moment about the mean) are calculated in real-time over a certain time-period, providing feedback about the level of arousal of the user in real-time. In principle no comparisons with previously measured baseline measurements or reference values are needed for an estimation of the level of arousal, such that calibrations are avoided. Also, no personal characteristics of a specific user need to be configured in advance.

These and other features make a computer program product, device and/or method according to the invention less obtrusive and suitable for various applications for humans and animals.

The computer program may be run on a computer, wherein the computer may comprise any computer, processing circuit or dedicated device such as an arousal measuring device or be incorporated in such a device. By use of the invention, the various applications, for example entertainment applications, may provide feedback and/or response to the user in a more pleasant way, or at least in a personally adapted way. Also GSR sensors can record GSR signals in a relatively non-obtrusive manner.

In a second aspect, said goal and/or other goals can be achieved individually or in combination by an arousal measuring device, provided with a GSR (galvanic skin response) sensor for recording GSR signals from a user, a processing circuit for processing the recorded GSR signals and a storage arrangement for storing the recorded and/or processed GSR signals and an algorithm, wherein the algorithm is configured to control the arousal measuring device to calculate a third or higher central moment of a recorded GSR signal and to derive an estimation of the level of arousal, or at least a change in the level of arousal, from said third or higher central moment.

In a third aspect, said goal and/or other goals can be achieved individually or in combination by a method for estimating a level of arousal, at least a change in the level of arousal, of a user, wherein GSR signals are received from a GSR sensor, wherein a third or higher central moment of a GSR signal is calculated, wherein said third or higher central moment is used to derive an estimation of the level of arousal, or at least a change in the level of arousal.

BRIEF DESCRIPTION OF THE DRAWINGS

In clarification of the invention, embodiments thereof will be further elucidated with reference to the drawing. In the drawing.

In this description, identical or corresponding parts have identical or corresponding reference numerals. The exemplary embodiments shown should not be construed to be limitative in any manner and serve merely as illustration.

DETAILED DESCRIPTION OF THE EMBODIMENTS

Figure 1:
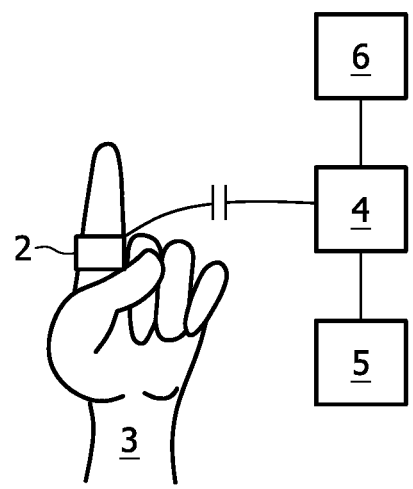
FIG. 1 shows a schematically illustrated arousal measuring device according to the invention.

FIG. 1 shows an arousal measuring device 1, provided with a GSR (galvanic skin response) sensor 2 for recording a GSR signal from the skin 3 of a user. In this embodiment a sensor 2 on the finger is shown by way of example only. The GSR sensor 2 may in principal be placed anywhere on the body, but preferably on a convenient place wherefrom reliable GSR measurements can be obtained. The GSR sensor 2 sends the GSR signal to a processing circuit 4 for processing these recorded GSR signals and a storage arrangement 5 for storing the recorded and/or processed GSR signals. The storage arrangement 5 also stores a computer program product having an algorithm that is configured to control the arousal measuring device 1, or at least the processing circuit 4 thereof, to process the GSR signals. In an embodiment, a human perceivable interface 6 is provided, which may, for example, be a display that in some way provides feedback on the basis of the measured state of arousal. A power source, not shown in the figure, feeds the electric components.

Said computer program product, or at least said algorithm, may run the device 1, or any computer, to make calculations based on the recorded GSR signal using a third or higher central moment. From the results of this statistical calculation an estimation of the level of arousal can be derived, as will be explained later.

The algorithm according to the invention is configured to use formulas, known in probability theory and statistics, that are characterised in this description as 'third or higher central moments'. Related to this, 'normalised third or higher central moments' may involve an extra calculating step and are dimensionless. Those should be understood as being comprised in 'third or higher central moments' as well. Other characterisations should also be understood as being included in the algorithm, such as for example, '(normalised) higher order moments about the mean', '(normalised) third or higher order measures', and '(normalised) third or higher order cumulant', etc. Sometimes when, in this context, a 'higher order moment' is stated, a 'third or higher order moment' is meant, and should also be understood to be comprised in the algorithm. A person skilled in the art will recognise like characterisations.

The third and fourth central moments are used to define skewness and kurtosis, respectively. In particular, the normalised third central moment and the normalised fourth central moment are called skewness and kurtosis, respectively, and are non-dimensional quantities. Also higher-order moments could be used within the scope of the invention.

The skewness characterises the degree of asymmetry of a distribution around its mean and characterises the shape of the distribution. Kurtosis measures the relative 'peakedness' or flatness of a distribution relative to a normal distribution. Skewness and kurtosis are usually defined as:

Skewness $[x_1 \ldots x_n] = (1/N) * \Sigma((x_j-\mu)/(\sigma)^3$, and

Kurtosis$[x_1, \ldots, x_n] = (1/N * \Sigma((x_j-\mu)/(\sigma)^4)-3$, respectively, wherein $\mu$=average $[x_1, \ldots, x_n] = (1/N) * \Sigma x_j$, and Variance=$\sigma^2$=Standard deviation$^2$ $[x_1, \ldots, x_n]=1/N * \Sigma(x_j-\mu)^2$.

From conducted experiments it appeared that a low measured skewness value indicated an increase in arousal and a high kurtosis value also indicated an increase in arousal. On the other hand, high skewness and low kurtosis relate to a decrease in arousal, i.e. an increase in relaxation. Thus, from the measured skewness and kurtosis of the GSR signal, the relative arousal state of a user can be derived. From the experiment it appeared that for measuring arousal by calculating the skewness and kurtosis, no calibration is needed before or during the experiment. Measured skewness and/or kurtosis results could be interpreted relatively directly.

Concepts directly related to arousal may for example be nervousness, excitement, stress, irritation, or the like. A person skilled in the art will recognise like emotions. The opposite of arousal could be described as relaxation, for example. Also for 'relaxation', a skilled person will understand that synonyms thereof or like emotions could be measured within the scope of the invention.

Figure 2:
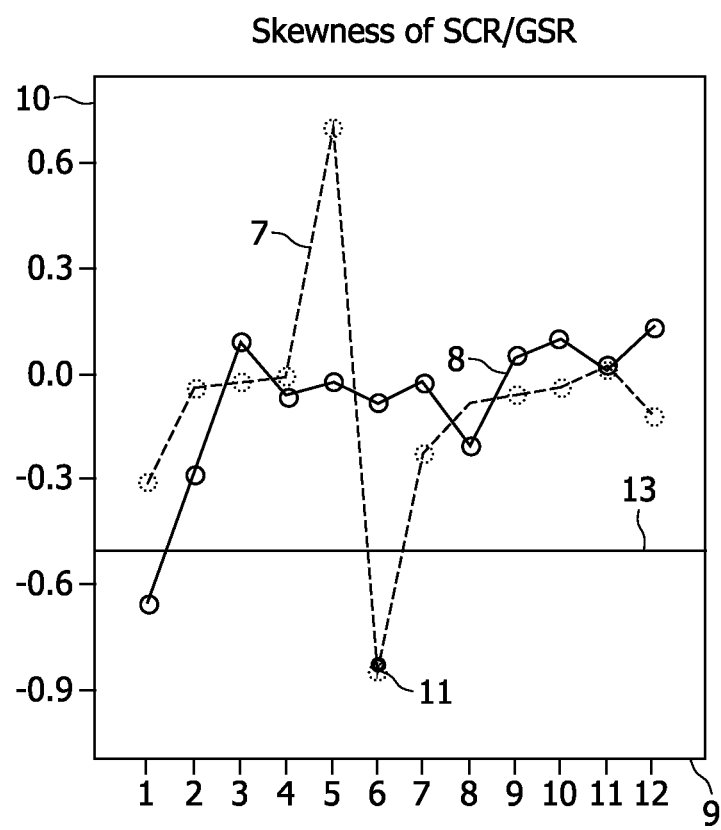
FIG. 2 shows a graph illustrating GSR signal skewness, varying over time.
Figure 3:
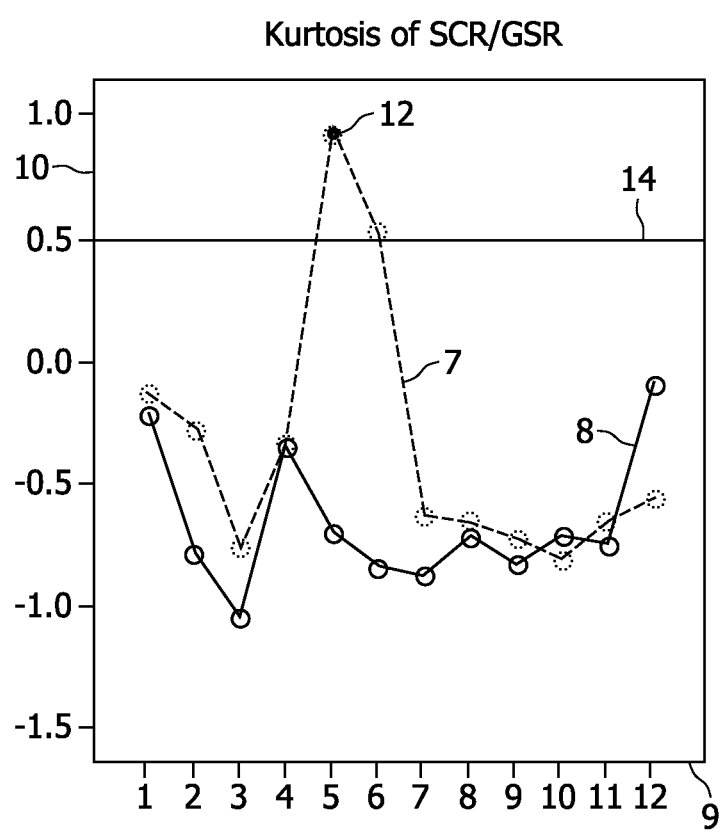
FIG. 3 shows a graph illustrating GSR signal kurtosis, varying over time.

Skewness and kurtosis were measured in an experiment wherein 22 subjects were tested. FIGS. 2 and 3 show the average scores for skewness and kurtosis, respectively, that were calculated for this experiment during the display of two 120-second movie fragments. For both figures, the horizontal axis 9 relates to the measured time, divided into twelve 10-second excerpts. The vertical axis 10 of FIGS. 2 and 3 corresponds to the calculated skewness and kurtosis value, respectively. In both figures, the dashed line 7 corresponds to a fragment of a film called 'Final destination' (2000, New Line Cinema), in which fragment unexpectedly a bus hits a student at approximately the 60$^{th}$ second. This 'scary surprise' can be derived from the dashed line 7. For skewness, in FIG. 2, the dashed line 7 shows a relatively low skewness score at approximately the 60$^{th}$ second, at point 11. For FIG. 3, there is a relatively high kurtosis score at point 12 at approximately 60 seconds, to be more exact the highest score is at 50 seconds. Both points 11, 12, at around seconds, e.g. between 50 and 70 seconds, indicate a high level of arousal corresponding with said 'scary surprise'. Thus a relatively high state of arousal can be derived from the (normalised) higher order central moment of the GSR signal, at least for skewness and kurtosis.

In FIGS. 2 and 3, the continued line 8 corresponds to a movie fragment from 'Lion King' (1994, Walt Disney) wherein one of the main movie characters looses his father. This fragment starts with a relatively increased tensional level and continues with a relatively steady tensional level. This increased and then steady tension can also be derived from the continued line 8 in both figures, starting at a relatively high tension, i.e. where skewness is low (FIG. 2) and kurtosis is high (FIG. 3) and continuing with a relatively steady course.

For the above-mentioned experiment, GSR skewness and kurtosis were measured over 10 second intervals. These intervals could also be shorter or longer. For example, 2.5 second or 60 second intervals could also be used. The choice of the interval may depend on the application. For example, for gaming industry relatively short intervals could be used, while for example for Yoga, the state of arousal could be measured for relatively longer periods. Needless to say, these examples should not be understood to be limiting to the invention.

In an embodiment, the algorithm is configured to control the computer to signal an increase in the level of arousal when the calculated skewness is below a threshold 13 of approximately −0.5 (see FIG. 2). This threshold 13 has been found to correspond with a more or less heightened level of arousal of the user, at least a relatively high increase in the level of arousal. However, also other values could be suitable to function as a threshold 13, e.g. −0.3 or −0.7. The choice of the threshold 13 value may for example depend on the application. In another embodiment, multiple thresholds 13 are used, indicating different levels of arousal, e.g. 0.3; 0.5 and 0.7. According to the same principle, the algorithm may be configured to control the computer to indicate a heightened level and/or an increase in the level of arousal when the calculated kurtosis is above a threshold 14 (see FIG. 3) of approximately 0.5, although a lower or higher threshold 14 may also be suitable, such as 0.3 or 0.7, for example. Also here, multiple thresholds 14 can be applied.

When the change in arousal, i.e. decrease or increase, exceeds a threshold 13, 14 the algorithm is configured to cause the processor to signal the perceivable interface 6 for providing sensory output to a user. For example, the user perceivable interface 6 may comprise a display and/or speaker system, signalling the user visually and/or through sound that his or her state of arousal is relatively high or low, i.e. has exceeded a threshold 13, 14. The user perceivable interface 6 may also be configured to respond to the measured state in a hardly noticeable manner, e.g. such that the user hardly notices that feedback is provided. In an example comprises a gaming station and is configured to respond in real-time to the received arousal state. By the invention, it is also possible to signal the arousal state in real-time, such that the gaming station, or any other embodiment of the invention, will react to the current state of the user, or at least with no more than a few seconds delay, for example. The delay can be just fractions of a second, several seconds, or whatever advantageous time period and/or may for example be dependent on what time intervals are used to calculate the third or higher central moment, or the normalised third or higher central moment. Embodiments of the invention can for example be connected to and/or embedded in various appliances such as for example relaxation products, entertainment industry, gaming industry, optimal performance of operators, biofeedback therapy, product evaluations, sports, simulations, etc.

In general the automated arousal measuring method according to the invention can for example be useful in areas where it may be relevant for a system to know the emotional state of the user and where it is advantageous to adapt feedback and functioning to it in an automated way, for example such that the emotional state of the user may be influenced in a reactive way, or to be able to read it, e.g. by a doctor such as a dentist or surgeon, etc. This adapted feedback and/or functioning may for example be brought in a way that is relatively non-obtrusive or less conscious for the user.

An embodiment of the invention is a game that gives extra points if the opponent of a user is brought into a state of stress or arousal, wherein the level of stress/arousal is measured in real-time. Also, the workload for factory operators could be adjusted based on the arousal measurements, so that these operators can function more optimally. In product evaluations for example, the level of stress relating to the use of a prototype could be read, e.g. such that the product may be improved based on the measurements. Obviously multiple of the like and other applications can be suitable within the scope of the invention.

If an embodiment of the invention is combined with other psychophysiological sensors that may be able to measure the psychophysiological state of a user, such that reliability of the results can be upgraded. For example in combination with heart beat sensors, e.g. for measuring the heart beat and/or the heart variability, muscle tension sensors, etc., the result of the GSR measurements can be upgraded. Also, multiple higher order central moments can be calculated for the same goal, such as e.g. skewness and kurtosis. Those measurements could be combined such that one measurement could confirm or contradict the other and a more reliable result may be obtained. For example for particular measurements, kurtosis as well as skewness should exceed a particular threshold in order to signal the user in a certain way.

It shall be obvious that the invention is not limited in any way to the embodiments that are represented in the description and the drawings. Many variations and combinations are possible within the framework of the invention as outlined by the claims. Combinations of one or more aspects of the embodiments or combinations of different embodiments are possible within the framework of the invention. All comparable variations are understood to fall within the framework of the invention as outlined by the claims.

The invention claimed is:

1. A non-transitory computer-readable medium encoded with instructions configured to control a processor of an arousal measuring device to perform a method comprising:
   receiving galvanic skin response signals in the processor of an arousal measuring device from a galvanic skin response sensor of the arousal measuring device;
   calculating a third or higher central moment of a galvanic skin response signal, wherein the third or higher order moment comprises at least one of: a skewness and a kurtosis;
   estimating at least one of: a level of arousal or a change in the level of arousal, wherein said estimation of the level of arousal is based on said calculated third or higher central moment exceeding a corresponding one of a plurality of threshold values, and wherein the estimation of the change in the level of a arousal is determined when one of:
   an increase in the level of arousal is determined when at least one of: a relatively low skewness or a relatively high kurtosis is calculated, or
   a decrease in the level of arousal is determined when at least one of: a relatively high skewness or a relatively low kurtosis is calculated; and
   outputting a signal to a user perceivable interface when one of: a level of arousal or a change in the level of arousal are estimated.

2. The medium of claim 1, wherein the medium comprises instructions to control the processor to signal to a user perceivable interface when at least one of:
   said change in the level of arousal is determined, or
   the level of arousal is derived.

3. The medium of claim 2, wherein the signal to the user perceivable interface is performed approximately immediately in real-time.

4. The medium of claim 1, wherein the increase in the level of arousal is derived when the calculated skewness is below a threshold of approximately −0.3.

5. The medium of claim 1, wherein the increase in the level of arousal is derived when the calculated kurtosis is above a threshold of approximately 0.3.

6. An arousal measuring device for processing galvanic skin response signals to estimate at least one of: a level of arousal or a change in the level of arousal of a user, said device comprising:
   a galvanic skin response sensor for providing galvanic skin response signals from a user body;
   a processing circuit for processing the provided galvanic skin response signals;
   a storage arrangement for storing at least one of the processed galvanic skin response signals;

wherein the processing comprises:
calculating a third or higher central moment of a recorded galvanic skin response signal, wherein the third or higher order moment comprises at least one of: a skewness and a kurtosis;
estimating at least one of: a level of arousal or a change in the level of arousal, wherein said estimation of the level of arousal is based on said calculated third or higher central moment exceeding a corresponding one of a plurality of threshold values, and wherein said change in the level of arousal is determined when one of:
an increase in the level of arousal is determined when at least one of: a relatively low skewness or a relatively high kurtosis is calculated, or
a decrease in the level of arousal is determined when at least one of: a relatively high skewness or a relatively low kurtosis is calculated.

7. The arousal measuring device of claim 6, further comprising:
a user perceivable interface for providing sensory output to a user.

8. The arousal measuring device of claim 6, further comprising:
a receiving system receiving measurements from other psychophysiological measuring devices configured for estimating an emotional state of a user.

9. An arousal measuring device, comprising:
a galvanic skin response sensor for providing galvanic skin response signals from a user,
a processing circuit configured to process the provided galvanic skin response signals,
a storage arrangement for storing at least one of the processed galvanic skin response signals,
the processor being configured to:
calculate a third or higher central moment of a provided galvanic skin response signal, wherein the third or higher order moment comprises at least one of: a skewness and a kurtosis; and
derive an estimation of at least one of the level of arousal or a change in the level of arousal, wherein said estimation of level of arousal is based on said calculated third or higher central moment exceeding a corresponding one of a plurality of threshold values, wherein an increase in the level of arousal is determined when at least one of: a relatively low skewness or a relatively high kurtosis is calculated, or a decrease in the level of arousal is determined when one of a relatively high skewness of a relatively low kurtosis is calculated.

10. A method, operable in an arousal measuring system, for estimating at least one of a level of arousal or a change in the level of arousal, of a user, the method comprising:
receiving galvanic skin response signals from a galvanic skin response sensor of the arousal measuring system,
using a processor of the arousal measuring system for calculating a third or higher central moment of the galvanic skin response signals, wherein the third or higher order moment comprises at least one of: a skewness and a kurtosis,
using the processor for deriving an estimate of at least one of the level of arousal and the change in the level of arousal, wherein said estimation of the level of arousal is based on said calculated third or higher central moment exceeding a corresponding one of a plurality of threshold values, and wherein said estimation of the change in the level of arousal is determined when one of: an increase in the level of arousal is determined when at least one of: a relatively low skewness or a relatively high kurtosis is calculated, or a decrease in the level of arousal is determined when one of a relatively high skewness or a relatively low kurtosis is calculated; and
the arousal measuring system outputting the estimate.

11. The method of claim 10, wherein the estimate of the level of arousal or change in the level of arousal is signaled to a user perceivable interface approximately immediately in real-time.

12. The method of claim 10, wherein an increase in the level of arousal is signaled when the calculated skewness is below a threshold of approximately −0.3.

13. The method of claim 10, wherein an increase in the level of arousal is signaled when the calculated kurtosis is above a threshold of approximately 0.3.

14. The method of claim 10, wherein an increase in the level of arousal is signaled when the calculated kurtosis is above a threshold of approximately 0.5.

15. The method of claim 10, wherein an increase in the level of arousal is signaled when the calculated skewness is below a threshold of approximately −0.5.

16. The non-transitory computer-readable medium of claim 1, wherein the increase in the level of arousal is signaled when the calculated skewness is below a threshold of approximately −0.5.

17. The non-transitory computer-readable medium of claim 1, wherein the increase in the level of arousal is indicated when the calculated kurtosis is above a threshold approximately 0.5.

* * * * *